United States Patent [19]

Celmer et al.

[11] 4,062,944
[45] Dec. 13, 1977

[54] MIXTURE OF ANTIBIOTICS PRODUCED BY NEW SPECIES OF MICROMONOSPORA

[75] Inventors: Walter D. Celmer; Frank C. Sciavolino, both of New London; Walter P. Cullen, East Lyme; John B. Routien, East Lyme, all of Conn.

[73] Assignee: Pfizer Inc., New York, N.Y.

[21] Appl. No.: 751,041

[22] Filed: Dec. 16, 1976

Related U.S. Application Data

[62] Division of Ser. No. 581,808, May 29, 1975, Pat. No. 4,013,789, which is a division of Ser. No. 431,845, Jan. 9, 1974, Pat. No. 3,914,218.

[51] Int. Cl.$^2$ .............................................. A61K 35/74
[52] U.S. Cl. .................................. 424/117; 195/80 R
[58] Field of Search ......................................... 424/117

[56] References Cited

U.S. PATENT DOCUMENTS 3,625,960  12/1971  Maggi .............................. 260/239.3

Primary Examiner—Jerome D. Goldberg
Attorney, Agent, or Firm—Connolly and Hutz

[57] ABSTRACT

A new species of Micromonospora, designated *Micromonospora lacustris* sp. nov. Routien, when subjected to submerged aerobic fermentation under controlled conditions, produces a mixture of at least 13 antibiotics. Two of these antibiotics are rifamycin S and rifamycin SV. Two other members of the antibiotic mixture are the 3-methylthio derivatives of rifamycin S and rifamycin SV.

1 Claim, 1 Drawing Figure

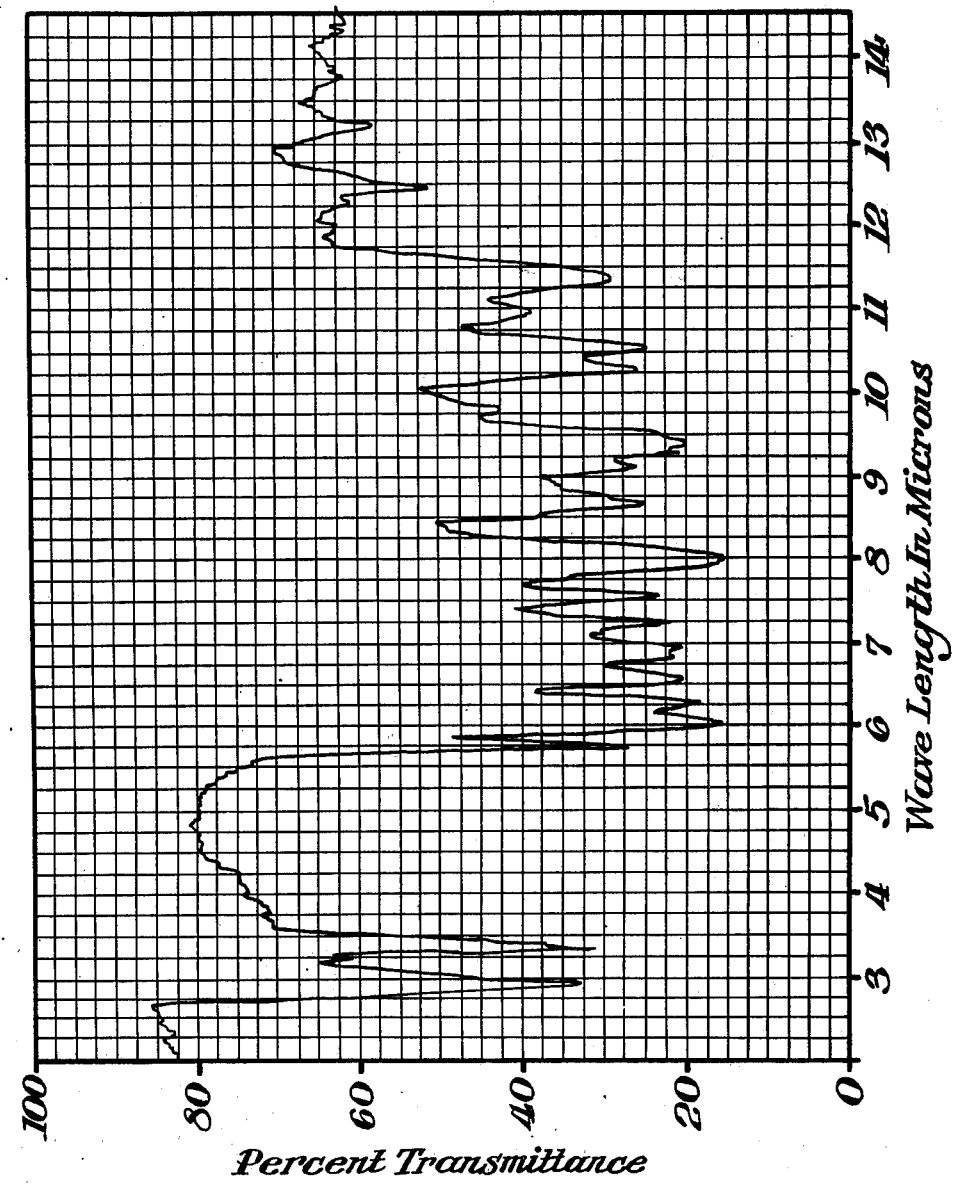

MIXTURE OF ANTIBIOTICS PRODUCED BY NEW SPECIES OF MICROMONOSPORA

CROSS REFERENCE TO RELATED APPLICATIONS

This application is a divisiion of application Ser. No. 581,808 filed May 29, 1975 now U.S. Pat. No. 4,013,789 which is a division of application Ser. No. 431,845 filed Jan. 9, 1974 l now U.S. Pat. No. 3,914,218.

BACKGROUND OF THE INVENTION

The rifamycins, a group of closely related antibiotics, are described by Sensi et al.: Farmaco, Ed. Sci. 14, 146 (1959); Antibiotics Ann. 1959/1960, 262 (1960a); Experientia 16, 412 (1960b); Framaco, Ed. Sci. 16, 165 (1961); and Res. Progr. Org. Biol. Med. Chem. 1, 337 (1964).

The constitution of the rifamycins was established by Prelog, V., Pure Appl. Chem. 7,511 (1963b). Prelog coined the term "ansamycin" to refer to this particular class of large molecule antibiotics.

SUMMARY OF THE INVENTION

This invention is concerned with a mixture of ansamycins produced by a new species of Micromonospora, designated *Micromonospora lacustris* sp. nov. Routien. Two members of the ansamycin mixture are rifamycin S and rifamycin SV. Two other ansamycins are the 3-methylthio derivatives of rifamycin S and rifamycin SV.

DETAILED DESCRIPTION OF THE INVENTION

The microorganism useful for the preparation of the antibiotics of this invention was isolated from a mud sample from Rogers Lake, Conn. This culture (Pfizer F.D. 23849), designated *Micromonospora lacustris* sp. nov. Routien, has been deposited in the American Type Culture Collection, Rockville, Md., and added to its collection, representative as the type culture as ATCC 21975.

Identification media used for the characterization of *M. lacustris* and references for their composition are as follows:

1. Bennett's Agar (and 0.1% $CaCO_3$)—Waksman, S.A. *The Actinomycetes* vol. 2, 1961. Medium 30 on p. 331.
2. Emerson's Agar (and 0.1% $CaCO_3$)—Waksman, 1961. Medium 28 on p. 331.
3. Tomato-Paste Oatmeal Agar (and 0.1% $CaCO_3$)—Waksman, 1961. Medium 34 on p. 332.
4. Glucose-Asparagine Agar (and 0.1% $CaCO_3$)—Waksman, 1961. Medium 2 on p. 328.
5. Glucose-Yeast Extract Agar (and 0.1% $CaCO_3$)—M. J. Weinstein et al. Antimicrobial Agents and Chemotherapy p. 436, 1968.
6. Starch
   (a) — Waksman, 1961. Medium 21 on p. 330.
   (b) — As above but with 1% yeast extract added.
   (c) — Gordon and Mihm, J. Bact. 73, 15–27, 1957.
   (d) — Potato starch 20.0 g.; Ammonium chloride 0.5 g.; Agar 15.0 g.; Distilled water 1.0 liter.
7. Gelatin — Waksman, 1961. Medium 20 on p. 330.
8. Tyrosine — Waksman, 1961. Medium 11 on p. 329.
9. Czapek-Sucrose — Waksman, 1961. Medium 1 on p. 328.
10. Potato Slice — Luedemann, G.M. and Brodsky, B., Antimicrobial Agents and Chemotherapy p. 47–52, 1965.
11. Potato Slice plus $CaCO_3$ — Luedmann and Brodsky, 1965.
12. Carrot Plugs.
13. Tap Water Agar (2%).
14. Peptone Iron Agar — Waksman, 1961. Medium 38 on p. 332.
15. Difco Skim Milk.
16. ATCC Medium 172 — ATCC Catalog of Strains, 9th Edition, p. 172, 1970.
17. Dextrose Nitrate Broth — Waksman, 1961. Medium 1 on p. 328. But with 3g glucose in place of sucrose and no agar.
18. Organic Nitrate Broth — Waksman, 1961. Medium 37 on p. 332.
19. Sucrose Invertase — Levine, M. and Schoenlein, H. W., A Compilation of Culture Media, 1930. Medium 622 on p. 176.
20. Cellulose — Levine and Schoenlein, 1930. Medium 2511 on p. 823.
21. Cellulose — Jensen, H. L., Proc. Linnean Soc. N.S. Wales 55, 231 (1930).
22. Nitrogen Utilization — Weinstein et al., Antimicrobial Agents and Chemotherapy p. 437, 1968.
23. Carbohydrate Utilization — Weinstein et al.

*M. lacustris* was planted in tubes or petri dishes at least in duplicate for some long range tests. Incubation was at 28° C. except where otherwise noted. Readings were made at various intervals up to 14 days with some tests continued for longer periods of time. The color designations refer to color of chips in "Color Harmony Manual," 4th edition, 1958, published by the Container Corporation of America, U.S.A., but descriptive terms are those of the investigator. The methods are mainly those described by M. J. Weinstein et al. in Antimicrobial Agents and Chemotherapy 435–437 (1967/1968). The description of *M. lacustris* ATCC 21975 is as follows:

Characteristic of the genus Micromonospora, *M. lacustris* has no aerial mycelium. There are spores only on the substrate mycelium, and these are borne singly on hyphae. Spores produced on tap water agar are rare, terminal, sessile, arranged at random in culture, mostly 1.1–1.5 microns wide, sometimes 2.0 microns wide. Infrequent intercalary swellings are found. On glucose-yeast extract agar the spores are similar but are sometimes numerous in brownish spots in the mycelium.

Yeast extract and NZ-Amine A (Sheffield Chemical Co.) provide for good growth. Sodium nitrate, asparagine and glutamic acid are not utilized. Growth is poor to good on ATCC Medium 172 at 21°, 28° and 37° C. but there is inconsistent growth at 45° C.

Nitrate reduction: no reduction of nitrate to nitrite in 21 days in either dextrose nitrate broth or organic nitrate broth.

$H_2S$ production: (4days, lead acetate strip test) — production from peptone iron agar.

Cellulose: no growth in either medium even after 38 days.

Gelatin: liquified.

Starch: no hydrolysis on media 6a and 6b but good hydrolysis on media 6c and 6d.

Sucrose inversion: positive.

Skimmed milk: no change at 21 days with later coagulation and partial peptonization occurring.

Carbon utilization: utilized—glucose, galactose, fructose, D-mannose, d(-) ribose, starch, sucrose, trehalose and xylose; not utilized—adonitol, L-arabinose, cellulose, dulcitol, inositol, D-mannitol, raffinose, rhammose and d(-) sorbitol; variable - lactose and D-melibiose.

Additional cultural data pertaining to *M. lacustris* ATCC 21975 are contained in the following table:

| Medium | Growth | Color of mycelium | Soluble pigment |
| --- | --- | --- | --- |
| Bennet's agar + CaCO$_3$ | Good, flat with some roughening | Bright orange (near 4 pa) | Bright yellow |
| Emerson's agar + CaCO$_3$ | Good, raised, roughened, wrinkled | Bright orange (5 pa to 5 pc) | Brown |
| Tomato paste oatmeal + CaCO$_3$ | Good to excellent, flat, smooth | Orange (4 pa to 5 ia) | Slight brown |
| Glucose-yeast extract + CaCO$_3$ | Moderate to good, flat or raised and roughened | Orange (4 na to 5 pa) | Brown |
| Glucose asparagine agar plus CaCO$_3$ | Essentially no growth | | |
| Czapek sucrose agar | Essentially no growth | | |
| Tyrosine agar | Essentially no growth | | |
| Potato slice | Good, roughened or thin, flat | Reddish orange (5 pc to 6 pa) | None |
| Potato slice + CaCO$_3$ | Good, wrinkled | Reddish orange None (near 5 pe) | |
| Gelatin | Poor to moderate, flat, thin | Pale yellowish orange (near 3 pe) | None |
| Carrot plugs | No growth | | |
| Starch agar | Essentially no growth on media 6a and 6b but good growth on 6e and 6d | | |

A mutant strain (Pfizer F.D. 24189), developed by mutagenic treatment of *M. lacustris* ATCC 21975, was deposited with the American Type Culture Collection and designated ATCC 21974. The mutant strain has a duller color than the parent culture on glucose-yeast agar plus CaCO$_3$ and other media. The mutant strain produces more spores and slightly larger spores than the parent culture. The mutant strain, in contrast to the parent culture, cannot utilize fructose and lactose as carbon sources. The mutant strain produces lesser amounts of rifamycin S and rifamycin SV in the employed fermentation media than does the parent culture.

Cultivation of *M. lacustris* preferably takes place in aqueous nutrient media at a temperature of about 24°–36° C., and under aerobic, submerged conditions with agitation. Nutrient media which are useful for such purposes include a source of assimilable carbon such as sugars, starch, glycerol and molasses; a source of organic nitrogen such as casein, enzymatic digest of casein, meat meal, wheat gluten, cotton seed meal, soybean meal and peanut meal. A source of growth substances such as distiller's solubles and/or yeast extract as well as salts such as sodium chloride, ammonium acetate, ammonium sulfate, potassium phosphate and trace minerals such as iron, magnesium, zinc, cobalt and manganese may also be utilized with advantageous results. If excessive foaming is encountered during fermentation, antifoam agents such as vegetable oils or silicones may be added to the fermentation medium. The pH of the fermentation tends to remain rather constant but if variations are encountered, a buffering agent such as calcium carbonate may also be added to the medium. Aeration of the medium in tanks for submerged growth is preferably maintained at the rate of about $\frac{1}{2}$ to 2 volumes of free air per volume of broth per minute. Agitation may be maintained by means of agitators generally familiar to those in the fermentation industry. Aseptic conditions must, of course, be maintained through the transfer of the microorganism and throughout its growth.

Inoculum for the preparation of the antibiotic mixture may be obtained by employing growth from slants of *M. lacustris* on such media as ATCC Medium 172 to which previous reference was made. The growth may be used to inoculate either shake flasks or inoculum tanks, or alternatively, the inoculum tanks may be seeded from the shake flasks. The growth of the microorganism usually reaches its maximum in about 2 or 3 days. However, variations in the equipment used, aeration, rate of stirring, and so forth, may affect the speed with which the maximum growth is reached. In general, the fermentation is conducted until substantial antimicrobial activity is imparted to the medium, a period of from about 24 hours to about 4 days being sufficient for most purposes.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency. After the fermentation broth has reached a level of antibiotic potency, the pH is usually about 7.5–8.5, the mycelium is removed by filtration or centrifugation. Various types of equipment such as filter presses, centrifuges, etc. may be employed.

Thin layer chromatography employing silica gel is a useful tool for analyzing the antibiotic mixture produced by *M. lacustris* in fermentation media and the composition of crude and purified materials extracted from clarified fermentation broths. The resolution of the components of the antibiotic mixture is importantly dependent on antibiotic loading of the system. Too little antibiotic potency fails to reveal minor antibiotic components; too much antibiotic potency results in a dragging effect with resulting poor resolution.

The developing system for the thin layer chromatography is the upper layer prepared from ethyl acetate, tetrahydrofuran and water (4:1:5). Bioautographic detection of the antibiotic components may be accomplished by means of an overlay of a thin layer of agar seeded with a sensitive strain of *Staphylococcus aureus* or other sensitive organism. The thin layer chromatograms, after development, may also be examined visually. The antibiotics present in the antibiotic mixture are all highly colored with various shades of orange, yellow and pink.

The rifamycins produced by *M. lacustris* are compounds of the formulae:

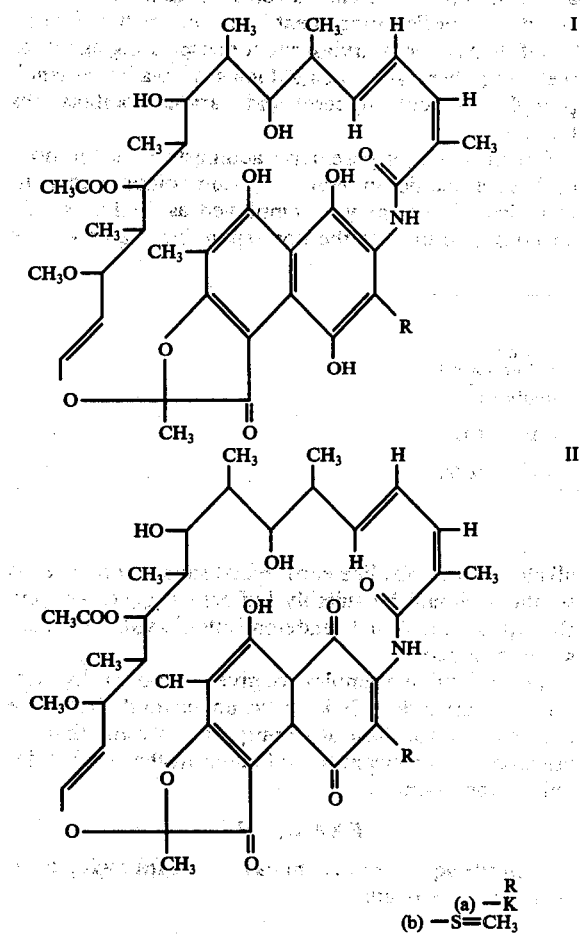

(a) —R
(b) —S=CH$_3$

The major portion (~ 90%) of the antibiotic mixture produced by *M. lacustris*, established by elemental analysis, mass spectrographic and nmr data, is represented by 3-methylthiorifamycin S (IIb) and 3-methylthiorifamycin SV (Ib). The largest minor components (~ 9%) are rifamycin S (IIa) and rifamycin SV (Ia). Smaller amounts of rifamycin S and rifamycin SV are produced by the mutant strain *M. lacustris* ATCC 21974.

In addition to the rifamycins, a new ansamycin designated Compound 32,656 is produced (~ 0.9%) and a number of other ansamycins in trace amounts totaling about 0.1% of the antibiotic mixture.

The oxidation-reduction equilibria established for rifamycin S and rifamycin SV exist for the 3-methylthio derivatives of these antibiotics. Rifamycin SV is oxidized by air or by manganese dioxide to rifamycin S. Rifamycin S is readily reduced to rifamycin SV by treatment with ascorbic acid. Similar oxidation-reduction reactions are operative for 3-methylthiorifamycin S and 3-methylthiorifamycin SV.

Hydrogenation of 3-methylthiorifamycin S in ethanol solution in the presence of 5% palladium on carbon until eight equivalents of hydrogen are consumed, removal of catalyst by filtration and evaporation of the filtrate yields the hexahydro derivative of 3-methylthiorifamycin SV. Oxidation of this compound with activated manganese dioxide gives the hexahydro derivative of 3-methylthiorifamycin S. Similarly, hydrogenation of Compound 32,656 gives the hexahydro derivative.

The components of the antibiotic mixture may be recovered from fermentation broth by a number of different procedures including solvent extraction and column chromatography or combinations thereof. Various organic solvents are useful in extracting the antibiotics from clarified broth. Methyl isobutyl ketone is a particularly effective solvent. Solvent extract is preferably carried out using a volume of solvent approximately equal to about one fifth the volume of broth from which it is desired to recover the antibiotic mixture. Depending on volumes of broth involved, various pieces of equpment such as separatory funnels, stirred tanks and mechanical extracting devices such as centrifugal separators are helpful for extraction purposes.

The ansamycins are preferably separated and isolated in the reduced state. This may be accomplished by adding ascorbic acid to the whole broth before filtration at a level of about 2 grams per gram of antibiotic mixture and stirring for about 30 minutes at room temperature. Alternatively, the antibiotics may be reduced with ascorbic acid at one of the solvent stages of recovery and concentration.

The preferred method of separation and recovery of the components of the antibiotic mixture is as follows: The clarified broth is adjusted to pH 4.0 to 4.5 and extracted with about 1/5 volume of methyl isobutyl ketone. The ketone is removed under vacuum and replaced with industrial ethanol. The ethanol solution is defatted by repeated extraction with petroleum ether. The ansamycins are reduced with ascorbic acid, the ethanol removed under vacuum and the residue taken up in chloroform. The chloroform is evaporated under vacuum and the residue is chromatographed on a silica gel column using ethyl acetate with increasing consentrations of acetone as the developing solvent. Column cuts are followed by thin layer chromatography and bioassay. The active cuts are combined accordingly. Compound 32,656 is in the fore cuts along with trace amounts of other ansamycins. The acetone concentration in the ethyl acetate-acetone developing mixture is raised stepwise to about 35–50%. The heart cut is eluted and concentrated yielding crystalline 3-methylthiorifamycin SV.

3-methylthiorifamycin SV is readily converted to 3-methylthiorifamycin S by oxidation with air or preferably by treatment with activated manganese dioxide which is prepared by azeotropic drying of manganese dioxide as described in J. Org. Chem. 34, No. 6, 1979 (1969). A slurry of activated manganese dioxide, approximately a gram per gram of antibiotic, is added to a methanolic or ethyl acetate solution of the antibiotic and stirred for about 30 minutes at room temperature at which time the oxidation is substantially complete. The reaction mixture is clarified by filtration or centrifugation and the solvent removed under vacuum.

The present invention includes within its scope the antibiotic products produced by *M. lacustris* in dilute forms, crude concentrates, and also the purified components thereof. All of these novel products are useful in combatting microorganisms, espcially *Mycobacterium tuberculosis, Diplocooccus pneumoniae, Streptococcus pyogenes* and *Staphylococcus aureus,* including strains which are resistant to other known antibiotics. In addition they are useful as disinfectants against such microorganisms and as an aid in the purification of mixed cultures for medical diagnostic and biological research purposes.

Table I illustrates the antibiotic spectra of some of these new ansamycins. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic (in micrograms/milliliter) at which the microorganism failed to grow. The tests were conducted under standardized conditions as described in Proc. Soc. Exp. Biol. & Med. 122, 1107 (1966). Tables II and III illustrate the in vivo activity of these new antibiotics in experimentally infected mice.

Table I

| Antibiotic | Minimal Inhibitory Concentration (ug/ml) | | | |
|---|---|---|---|---|
| | M. tuber. H Rv 37 | Streptococcus pyogenes | Staphylococcus aureus | S. aureus (multi-resistant) |
| 3-methylthio-rifamycin SV | 0.015 | 0.0019 | 0.0019 | 0.0019–0.0039 |
| 3-methylthio-rifamycin S | 0.006 | 0.0009 | 0.0004 | 0.0012–0.0039 |
| Compound 32,656 | 0.1 | 0.0312 | 0.0039 | 0.0012–0.0078 |

Table II

| Antibiotic | $PD_{50}$, mg/kg* | | | |
|---|---|---|---|---|
| | Diplococci oral | Streptococci oral | oral | Staphylococci subcutaneous |
| 3-methylthio rifamycin SV | 8.0 | 0.22 | 1.1 | 0.65 |
| 3-methylthio rifamycin S | >12.5 | 0.60 | 1.4 | 0.17 |
| Compound 32,656 | | | 1.15 | |

*Dose that provides 50% protection

Table III

| | M. tuberculosis Infection in Mice | | |
|---|---|---|---|
| | Daily Dose (mg) | Percent Survival* | Average Survival Time (days)* |
| 3-methylthio-rifamycin SV | 5.0 | 100 | 53.0 |
| | 0.5 | 70 | 44.3 |
| Control | 0 | 20 | 37.7 |

*Evaluated at 53 days post challenge

The antibiotics of these inventions can be administered via the oral or parenteral routes for the treatment in animals, including humans, of pneumococcal, streptococcal, staphylococcal, tubercular and other antibiotic-sensitive infections. In general, these antibiotics are most desirably administered in daily oral doses of 0.5–1 gram or parenteral injections of 100 to 500 mg., depending on the type and severity of the infection and weight of the subject being treated.

The compounds of this invention may be administered alone or in combination with pharmaceutically-acceptable cariers, and such administration can be carried out in both single and multiple doses.

For purposes of oral administration, tablet containing various excipients such as sodium citrate, calcium carbonate and dicalcium phosphate may be employed along with various disintegrants such as starch, alginic acid and certain complex silicates together with binding agents such as polyvinylpyrollidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspensions and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purposes of parenteral administration, solutions of these antibiotics in sesame or peanut oil or in aqueous propylene glycol may be employed as well as sterile aqueous solutions of the corresponding water-soluble alkali metal or alkaline-earth metal salts. Such aqueous solutions should be suitably buffered if necessary and the liquid diluent first rendered isotonic with sufficient saline or glucose.

The following examples are given to more fully illustrate the invention. It is to be understood that these examples are for illustrative purposes only and that the invention is not meant to be limited to the specific details of the examples.

EXAMPLE I

A sterile aqueous medium having the following composition is prepared:

| | Grams/liter |
|---|---|
| Starch | 20.0 |
| Enzymatic digest of casein | 5.0 |
| Yeast extract | 5.0 |
| Dextrose | 10.0 |
| $K_2HPO_4$ | 0.5 |
| $CaCO_3$ | 4.0 |

Cells from a slant of M. lacustris ATCC 21975 are transferred to a series of 3-liter Fernbach flasks each containing a liter of this medium and shaken for 3–4 days at 28° C.

About 1% v/v of the grown inoculum is transferred to a fermenter containing 150 gallons of sterile medium of the following composition:

| | Grams/liter |
|---|---|
| Starch | 25.0 |
| Enzymatic digest of casein | 15.0 |
| dl-Methionine | 1.0 |
| Ammonium acetate | 0.5 |
| Ammonium sulfate | 0.1 |
| $K_2HPO_4$ | 0.4 |
| Sucrose | 1.0 |
| $CaCO_3$ | 4.0 |
| Meat meal | 10.0 |
| $FeSO_4 . 7H_2O$ | 0.02 |
| $MgSO_4 . 7H_2O$ | 0.1 |
| $ZnSO_4 . 7H_2O$ | 0.002 |
| $MnCl_2$ | 0.002 |

|  | Grams/liter |
|---|---|
| $CoCl_2 \cdot 6H_2O$ | 0.002 |

The temperature is maintained at about 30° C. and the broth is stirred at 1150 rpm and aerated at the rate of ½ volume of air per volume of broth per minute. After 35–45 hours, 5% v/v of this grown inoculum is transferred to a fermenter containing 1000 gallons of the sterile medium described above. The temperature is maintained at 30° C., aeration at ½ volume of air per volume of broth per minute and stirring at 600 rpm. Soybean oil is added as needed to control excessive foaming. After 50–60 hours, 5–10% v/v of this grown inoculum is transferred to a fermenter containing 10,000 gallons of sterile medium which is the same as that described above but without meat meal. The temperature is maintained at 30° C., aeration at the rate of ½ volume of air per volume of broth per minute and stirring at 380 rpm. Soybean oil is added as necessary to control foam. Sucrose or dextrose is added at 24 hour intervals to a level of about 0.1% w/v.

After 90–120 hours, the fermentation broth is filtered and the pH adjusted to 4.0–4.5 in the presence of 5–10% methyl isobutyl ketone. The broth is then extracted with 2500 gallons of methyl isobutyl ketone by means of a Podbielniak extractor and centrifugal separator. The solvent extract is concentrated under vacuum to 1/10–1/20 volume and the pH adjusted to 5.5–6.5 with ammonia or 10% $K_2HPO_4$ solution.

The solvent (approximately 200 gallons) is removed under vacuum and replaced with 3A ethanol. The ethanol solution is concentrated under vacuum to about 20 gallons which is defatted by repeated extraction with petroleum ether. To the ethanolic solution is added ascorbic acid (about 2 grams/gram of antibiotic mixture) and the solution is stirred at room temperature for about 30 minutes. The ethanolic solution is concentrated under vacuum, maintaining the pH at 6–7 if necessary, to a thin syrup which is then taken up in chloroform.

The chloroform solution is concentrated to a syrup which is then chromatographed on a silica gel column and developed with ethyl acetate containing increasing 5% increments of acetone. The column cuts are followed by thin layer chromatography and bioassay, and the cuts are combined accordingly. The fore cuts contain Compound 32,656 and trace amounts of rifamycin S, rifamycin SV and other ansamycins. The heart cut eluate when concentrated yields crystalline 3-methylthiorifamycin SV.

EXAMPLE II

The method of Example I is repeated with *M. lacustris* ATCC 21974 in place of ATCC 21975. Comparable results are obtained except for the fermentation production of smaller amounts of rifamycin S and rifamycin SV.

EXAMPLE III

A dry solid pharmaceutical composition is prepared by blending the following maerials together in the proportions by weight specified below:

| | |
|---|---|
| 3-Methylthiorifamycin SV | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 500 mg. of the active ingredient. Other tablets are prepared in a similar manner containing 250, 100 and 50 mg. of the active ingredient by using the appropriate amount of 3-methylthiorifamycin SV in each case.

EXAMPLE IV

Vials are prepared containing weighed amounts of the sterile sodium salt of 3-methylthiorifamycin SV. These vials are reconstituted for parenteral administration to 100 or 200 mg/ml with sterile water or 5% dextrose solution.

EXAMPLE V

Analytical Data

| 3-Methylthiorifamycin S | |
|---|---|
| Carbon | 61.48 |
| Hydrogen | 6.70 |
| Nitrogen | 1.90 |
| Sulfur | 4.15 |

Mass spectrometer and nmr data are consistent with 3-thiomethylrifamycin S ($C_{38}H_{47}O_{12}NS$). Its ultraviolet absorption maxima in 0.01 M HCl in methanol solution occur at 200, 265, 309 and 373 $\mu$.

A KBr pellet shows characteristic absorption in the infrared region at the following wavelengths in microns: 2.90, 3.40, 5.70, 5.80, 5.95, 6.15, 6.35, 6.80, 7.05, 7.25, 7.60, 7.75, 8.00, 8.40, 8.55, 8.90, 9.30, 9.50, 10.30, 10.60. 10.80, 11.20 and 12.00.

| 3-Methylthiorifamycin SV (sodium salt) | |
|---|---|
| Carbon | 56.24 |
| Hydrogen | 6.47 |
| Nitrogen | 1.59 |
| Sulfur | 3.50 |

Mass spectrometer and nmr data are consistent with the sodium salt of 3-thiomethylrifamycin SV ($C_{38}H_{48}NaO_{12}NS$). Its ultraviolet light absorption maxima in 0.01 M HCl in methanol solution occur at 225, 305 and 440 $\mu$.

A KBr pellet shows characteristic absorption in the infrared region at the following wavelengths in microns: 2.90, 3.40, 5.25, 5.95, 6.50, 7.00, 7.25, 7.55, 8.15, 8.70, 9.30, 9.45, 10.30, 10.65, 11.35, 12.50, 12.80, 13.30 and 13.75.

Rifamycin S

The identity of rifamycin S produced by *M. lacustris* was established by elementary analysis and comparisons with published infrared and ultraviolet light absorption spectra.

Rifamycin SV

The identity of rifamycin SV produced by *M. lacustris* was established by elementary analysis and comparisons of infrared and ultraviolet light absorption spectra with published data.

| Compound 32,656 | |
| --- | --- |
| Carbon | 58.19% |
| Hydrogen | 5.97% |
| Nitrogen | 3.17% |
| Sulfur | 3.52% |
| Oxygen (by difference) | 29.15% |

The compound is slightly soluble in water and petroleum ether and readily soluble in methanol, ethanol, acetone and ethyl acetate.

Its ultraviolet light absorption maxima in 0.01 M HCl in methanol solution occur at 225, 253 (inflection), 300 and 414 $\mu$ with $E_{1\%}$ values of 465, 280, 290 and 150 respectively. When pelleted in KBr (infrared spectrum attached) characteristic absorption in the infrared region occur at the following wavelengths in microns: 2.90, 3.40, 5.75, 6.05, 6.30, 6.60, 6.80, 6.95, 7.25, 7.55, 7.95, 8.65, 9.40, 10.25, 10.55, 11.35, 12.45 and 13.20.

EXAMPLE VI

Hydrogenation of an ethanolic solution of 3-methylthiorifamycin S in the presence of 5% palladium on carbon until 8 equivalents of hydrogen are consumed) removal of the catalyst by filtration and evaporation of the filtrate yielded the hexahydro derivative of 3-methylthiorifamycin SV, identified by mass spectrometer data. Oxidation of this compound with activated manganese dioxide yields hexahydro-3-methylthiorifamycin S. The antibiotic properties of these hexahydro derivatives are comparable to those of the parent compounds.

EXAMPLE VII

The hexahydro derivative of Compound 32,656, with antibiotic activity comparable to that of the parent compound, is prepared by hydrogenating Compound 32,656 by the method of Example VI.

What is claimed is:

1. Antibiotic substance Compound 32,656 which in crystalline form dissolved in 0.01 M HCl in methanol exhibits absorption maxima in the ultraviolet light region of the spectrum at 225, 253 (inflection), 300 and 414 $\mu$ with $E_{1\%}$ values of 465, 280, 290 and 150 respectively; having the average composition by weight of 58.19% carbon, 5.97% hydrogen, 3.17% nitrogen, 3.52% sulfur and 29.15% oxygen (by difference); and when pelleted in KBr exhibits characteristic absorption in the infrared region at the following wavelengths in microns: 2.90, 3.40, 5.75, 6.05, 6.30, 6.60, 6.80, 6.95, 7.25, 7.55, 7.95, 8.65, 9.40, 10.25, 10.55, 11.35, 12.45 and 13.20.

* * * * *